(12) United States Patent
Grunenberg et al.

(10) Patent No.: US 9,957,232 B2
(45) Date of Patent: May 1, 2018

(54) 4-[4-({[4-CHLORO-3-(TRIFLUOROMETHYL)PHENYL]CARBAMOYL}AMINO)-3-FLUOROPHENOXY]-N-METHYLPYRIDINE-2-CARBOXAMIDE MONOHYDRATE

(75) Inventors: Alfons Grunenberg, Dormagen (DE); Juergen Stiehl, Sprockhövel (DE); Katharina Tenbieg, Dortmund (DE); Birgit Keil, Düsseldorf (DE)

(73) Assignee: BAYER HEALTHCARE LLC, Whippany, NJ (US)

( * ) Notice: Subject to any disclaimer, the term of this patent is extended or adjusted under 35 U.S.C. 154(b) by 1745 days.

(21) Appl. No.: 12/444,974

(22) PCT Filed: Sep. 29, 2007

(86) PCT No.: PCT/EP2007/008503
§ 371 (c)(1),
(2), (4) Date: Mar. 4, 2010

(87) PCT Pub. No.: WO2008/043446
PCT Pub. Date: Apr. 17, 2008

(65) Prior Publication Data
US 2010/0173953 A1    Jul. 8, 2010

(30) Foreign Application Priority Data
Oct. 11, 2006 (EP) .................................... 06021296

(51) Int. Cl.
| C07D 213/78 | (2006.01) |
| C07D 213/81 | (2006.01) |
| C07D 213/62 | (2006.01) |
| A61K 45/06  | (2006.01) |
| A61K 31/44  | (2006.01) |

(52) U.S. Cl.
CPC ............ *C07D 213/78* (2013.01); *A61K 31/44* (2013.01); *A61K 45/06* (2013.01); *C07D 213/62* (2013.01); *C07D 213/81* (2013.01)
USPC .......................................... 546/298; 514/351

(58) Field of Classification Search
CPC .. C07D 231/78; C07D 213/81; C07D 213/62; A61K 31/44; A61K 45/06
See application file for complete search history.

(56) References Cited

U.S. PATENT DOCUMENTS

| 4,223,153 | A  | 9/1980  | Lappas et al. |
| 4,812,561 | A  | 3/1989  | Hamashima et al. |
| 4,835,180 | A  | 5/1989  | Schlegel et al. |
| 5,011,472 | A  | 4/1991  | Aebischer |
| 5,023,252 | A  | 6/1991  | Hseih |
| 5,629,425 | A  | 5/1997  | LaBell et al. |
| 6,140,321 | A  | 10/2000 | Imai et al. |
| 6,187,799 | B1 | 2/2001  | Wood et al. |
| 6,337,396 | B1 | 1/2002  | Kumar et al. |
| 6,344,476 | B1 | 2/2002  | Ranges et al. |
| 7,235,576 | B1 | 6/2007  | Riedl et al. |
| 7,329,670 | B1 | 2/2008  | Dumas et al. |
| 7,351,834 | B1 | 4/2008  | Riedl et al. |
| 7,371,763 | B2 | 5/2008  | Dumas |
| 7,517,880 | B2 | 4/2009  | Miller et al. |
| 7,528,255 | B2 | 5/2009  | Riedl et al. |
| 7,557,129 | B2 | 7/2009  | Scott et al. |
| 7,625,915 | B2 | 12/2009 | Dumas et al. |
| 7,678,811 | B2 | 3/2010  | Dumas et al. |
| 7,838,524 | B2 | 11/2010 | Lee et al. |
| 7,838,541 | B2 | 11/2010 | Dumas et al. |
| 7,897,623 | B2 | 3/2011  | Riedl et al. |
| 7,928,239 | B2 | 4/2011  | Dumas et al. |
| 7,928,277 | B1 | 4/2011  | Cox, Jr. |
| 8,071,616 | B2 | 12/2011 | Dumas et al. |
| 8,076,488 | B2 | 12/2011 | Dumas et al. |
| 8,101,773 | B2 | 1/2012  | Smith et al. |
| 8,110,587 | B2 | 2/2012  | Dumas et al. |
| 8,124,630 | B2 | 2/2012  | Riedl et al. |
| 8,124,782 | B2 | 2/2012  | Logers et al. |
| 8,207,166 | B2 | 6/2012  | Lee et al. |
| 8,217,061 | B2 | 7/2012  | Gavenda et al. |
| 2002/0042517 | A1 | 4/2002  | Khire et al. |
| 2003/0207872 | A1 | 11/2003 | Riedl et al. |
| 2003/0216446 | A1 | 11/2003 | Dumas et al. |
| 2004/0229937 | A1 | 11/2004 | Dumas et al. |
| 2005/0038080 | A1 | 2/2005  | Boyer et al. |
| 2005/0059703 | A1 | 3/2005  | Wilhelm et al. |
| 2006/0034797 | A1 | 2/2006  | Arien et al. |
| 2006/0058358 | A1 | 3/2006  | Dumas et al. |
| 2006/0078617 | A1 | 4/2006  | Schueckler |
| 2006/0247186 | A1 | 11/2006 | Carter et al. |
| 2007/0020704 | A1 | 1/2007  | Wilhelm et al. |
| 2007/0105142 | A1 | 5/2007  | Wilhelm |

(Continued)

FOREIGN PATENT DOCUMENTS

| GB | 1216714 B    | 3/1968 |
| WO | WO 1996-09045 | 3/1996 |

(Continued)

OTHER PUBLICATIONS

Battacharya, S. in Brittain, H. ed., Polymorphism in Pharmaceutical Solids, Informa Healthcare USA 2009, p. 334.*
Bhattacharya excerpt fr Brittain, H. ed., Polymorphism in Pharmaceutical SolidsDrugs and the Pharmaceutical Sciences; V. 95 New York Marcel Dekker, Inc., 1999.*
Ivanisevic, I. Pharm. Form. Qual. 2011, pp. 30-33.*
Ivanisevic, I., Pharm. Form. Qual. 2011, pp. 30-33.*
Brittain, H., ed., Polymorphism in Pharmaceutical Solids 2009 NY Informa Healthcare USA, pp. 318-335.*

(Continued)

*Primary Examiner* — Heidi Reese
(74) *Attorney, Agent, or Firm* — Millen White Zelano & Branigan, PC

(57) ABSTRACT

The present invention relates to 4-[4-({[4-chloro-3-(trifluoromethyl)phenyl]carbamoyl}amino)-3-fluorophenoxy]-N-methylpyridine-2-carboxamide monohydrate, to processes for its preparation, to pharmaceutical compositions comprising it and to its use in the control of disorders.

29 Claims, 7 Drawing Sheets

(56) References Cited

U.S. PATENT DOCUMENTS

| | | |
|---|---|---|
| 2007/0178494 A1 | 8/2007 | Elting et al. |
| 2007/0244120 A1 | 10/2007 | Dumas et al. |
| 2008/0032979 A1 | 2/2008 | Riedl et al. |
| 2008/0045546 A1 | 2/2008 | Bouchon et al. |
| 2008/0045589 A1 | 2/2008 | Kelley |
| 2008/0108672 A1 | 5/2008 | Riedl et al. |
| 2008/0153823 A1 | 6/2008 | Riedl et al. |
| 2008/0194580 A1 | 8/2008 | Dumas et al. |
| 2008/0227828 A1 | 9/2008 | Dumas et al. |
| 2008/0242707 A1 | 10/2008 | Schuckler et al. |
| 2008/0269265 A1 | 10/2008 | Miller et al. |
| 2008/0300281 A1 | 12/2008 | Dumas et al. |
| 2008/0311601 A1 | 12/2008 | Elting et al. |
| 2009/0068146 A1 | 3/2009 | Wilhelm |
| 2009/0093526 A1 | 4/2009 | Miller et al. |
| 2009/0118268 A1 | 5/2009 | Riedl et al. |
| 2009/0176791 A1 | 7/2009 | Sandner et al. |
| 2009/0192127 A1 | 7/2009 | Scheuring et al. |
| 2009/0192200 A1 | 7/2009 | Gavenda et al. |
| 2009/0215833 A1 | 8/2009 | Grunenberg et al. |
| 2009/0215835 A1 | 8/2009 | Wilhelm |
| 2009/0221010 A1 | 9/2009 | Elting et al. |
| 2009/0227637 A1 | 9/2009 | Weber et al. |
| 2009/0306020 A1 | 12/2009 | Scheuring et al. |
| 2010/0035888 A1 | 2/2010 | Sandner et al. |
| 2010/0063088 A1 | 3/2010 | Wood et al. |
| 2010/0063112 A1 | 3/2010 | Grunenberg et al. |
| 2010/0075971 A1 | 3/2010 | Dumas et al. |
| 2010/0081812 A1 | 4/2010 | Smith et al. |
| 2010/0113533 A1 | 5/2010 | Stiehl et al. |
| 2010/0129321 A1 | 5/2010 | Weber et al. |
| 2010/0144749 A1 | 6/2010 | Wilhelm |
| 2010/0150863 A1 | 6/2010 | Smith et al. |
| 2010/0160371 A1 | 6/2010 | Ranges et al. |
| 2010/0173953 A1 | 7/2010 | Grunenberg et al. |
| 2010/0173954 A1 | 7/2010 | Wilhelm et al. |
| 2010/0267777 A1 | 10/2010 | Wilhelm et al. |
| 2011/0015195 A1 | 1/2011 | Dumas et al. |
| 2011/0136809 A1 | 6/2011 | Lee et al. |
| 2011/0158942 A1 | 6/2011 | Weber et al. |
| 2011/0178137 A1 | 7/2011 | Albrecht-Kupper et al. |
| 2011/0195110 A1 | 8/2011 | Smith et al. |
| 2011/0257035 A1 | 10/2011 | Pena et al. |
| 2012/0009150 A1 | 1/2012 | Weber et al. |
| 2012/0040925 A1 | 2/2012 | Carter et al. |
| 2012/0040986 A1 | 2/2012 | Riedl et al. |
| 2012/0046290 A1 | 2/2012 | Miller et al. |
| 2012/0129893 A1 | 5/2012 | Dumas et al. |
| 2012/0142741 A1 | 6/2012 | Schueckler |
| 2012/0142742 A1 | 6/2012 | Riedl et al. |
| 2012/0149706 A1 | 6/2012 | Dumas et al. |
| 2012/0264789 A1 | 10/2012 | Jaryal et al. |
| 2013/0005777 A1 | 1/2013 | Jaryal et al. |

FOREIGN PATENT DOCUMENTS

| | | |
|---|---|---|
| WO | WO 1998-11893 | 3/1998 |
| WO | WO 2000-42012 | 7/2000 |
| WO | 01/51919 A2 | 7/2001 |
| WO | WO 2003-047579 | 6/2003 |
| WO | WO 2003-068228 | 8/2003 |
| WO | WO 2005-000284 | 1/2005 |
| WO | 2005/009961 A2 | 2/2005 |
| WO | 2005009961 A2 | 2/2005 |
| WO | 2005/077945 A2 | 8/2005 |
| WO | 2006026500 A1 | 3/2006 |
| WO | WO 2006-026500 | 3/2006 |
| WO | WO 2006-034796 | 4/2006 |
| WO | WO 2006-094626 | 9/2006 |
| WO | 2006125540 A1 | 11/2006 |
| WO | PCTEP0708503 R | 2/2008 |
| WO | WO 2008-043446 | 4/2008 |
| WO | WO 2008-058644 | 5/2008 |
| WO | WO 2011/0146725 | 11/2011 |
| WO | WO 2012 012404 | 1/2012 |
| WO | WO 2010/0048304 | 4/2012 |

OTHER PUBLICATIONS

Calabresi, Paul and Bruce A. Chabner. "Chemotherapy of Neoplastic Diseases." (The Pharmacological Basis of Therapeutics), 1996, 1225-1232.

Chabner, Bruce A. et al. "Antineoplastic Agents." (NIOSH) 1996, 1233-1287.

Noble et al., "Protein Kinase Inhibitors: Insights into Drug Design From Structure," Science, (2004), vol. 303, pp. 1800-1805.

Gelasser, "The Importance of Solvates," in: Polymorphism in the Pharmaceutical Industry, Chapter 8, p. 211, 2006, Wiley-VCH Verlug GmbH & Co., KGaA, Weinhelm.

Powell, M.F., et al. "Compendium of Excipients for Parenteral Formulations," PDA Journal of Pharmaceutical Science & Technology (1998), 52(5), 238-311.

Strickley, R.G., "Parenteral Formulations of Small Molecule Therapeutics Marketed in the United States (1999)-Part-I," PDS Journal of Pharmeceutical Science & Technology (1999), 53(6), 324-439.

Nema, S., et al., "Excipients and Their Use in Injectable Products," PDS Journal of Pharmaceutical Science & Technology, (1997), 51(4), 166-171.

Braga, et al., "Crystal Polymorphism: Challenges at the Crossroads of Science and Technology," Making Crystals by Design, Edited by Dario Braga and Fabrizia Grepioni, Copyright © 2007 Wiley-VCH, ISBN: 978-3-527-31506-2.

Threlfall, T.L., "Analysis of Organic Polymorphs—A Review," Anaylst, Oct. 1995, vol. 120, 2435-2460.

Battacharya, S., in Brittain, H. ed., "Polymorphism in Pharmaceutical Solids," Informa Healthcare USA, p. 334.

Claims of U.S. Appl. No. 11/956,111, filed Dec. 13, 2007.

Claims and Office Action of U.S. Appl. No. 11/845,595, filed Aug. 27, 2007.

Claims of U.S. Appl. No. 13/368,812, filed Feb. 8, 2012.

Claims of U.S. Appl. No. 13/208,010, filed Aug. 11, 2011.

Claims and Office Action of U.S. Appl. No. 12/514,715, filed May 13, 2009.

Claims and Office Action of U.S. Appl. No. 12/444,974, filed Apr. 9, 2008.

Claims and Office Action of U.S. Appl. No. 12/514,129, filed May 8, 2009.

Claims and Office Action of U.S. Appl. No. 11/664,363, filed Jun. 20, 2008.

Claims and Office Action of U.S. Appl. No. 10/895,985, filed Jul. 22, 2004.

Pending U.S. Appl. No. 13/368,812, filed Feb. 8, 2012.

Bankston et al., "A Scaleable Synthesis of BAY 43-9006: A Potent Raf Kinase Inhibitor for the Treatment of Cancer," Organic Process Research & Development, 2002, vol. 6, pp. 777-781.

Gura, "Systems for identifying new drugs are often faulty." Science, 1997, vol. 278 (5340), pp. 1041-1042.

Patani, G.A., et. al., "Bioisosterism: A Rational Approach in Drug Design," Chem. Rev., 96, 1996, pp. 3147-3176.

Gray, N.S., et al., "Exploiting chemical libraries, structure, and genomics in the search for kinase inhibitors," Science, 281, 1998, pp. 533-538.

Wang, Z., et al., "Structural basis of inhibitor selectivity in MAP kinases," Structure, 6, 1998, pp. 1117-1128.

Kelly, T.R., et al., "Relative Binding Affinity of Carboxylate and Its Isosteres: Nitro, Phosphate, Phosphonate, Sulfonate, and _-Lactone," J. Am. Chem. Soc., 116, 1994, pp. 7072-7080.

Mann, J., "Modern Methods for the Introduction of Fluorine into Organic Molecules: An Approach to Compounds with Altered Chemical and Biological Activities," Chem. Soc. Rev., 16, 1987, pp. 381-436.

Filler, R., et al., Organo-fluorine Compounds in Medicinal and Biomedical Applications, Eds., Elsevier; Amsterdam, 1993. Cover and Table of Contents (2 pages).

(56) References Cited

OTHER PUBLICATIONS

Wilhelm, S., et al., "Discovery and development of sorafenib: a multikinase inhibitor for treating cancer," Nature Reviews Drug Discovery, 5, Oct. 2006, pp. 835-844.
Jeffcoat, A. R. et al., "The Metabolism and Toxicity of Halogenated Carbanilides . . . " Drug Metabolism and Disposition, 5, 2, Aug. 19, 1976, pp. 157-166.
Riedl, B., et al., "Potent Raf Kinase Inhibitors from the Diphenylurea Class: Structure Activity Relationships," PD, 3, 2001, p. 923, Abstract # 4956.
Hansch, Corwin & Unger, Stefan, "Strategy in Drug Design. Cluster Analysis as an Aid in the Selection of Substituents," 16 J. Med. Chem. 1217 (1973).
Hodgetts, Kevin, et al., "The Role of Fluorine in the Discovery & Optimization of CNS Agents: Modulation of Drug-Like Properties," 45 Ann. Reports in Med. Chem. 429 (2010).
Isanbor, C., "Fluorine in Med. Chem: A Review of Anti-Cancer Agents," 127 J. of Fluorine Chem. 303 (2006).
O'Hagan, D., "Some Influences of Fluorine in Bioorganic Chemistry," 645 Chem. Commun. (1997).
Pleiss, U., et al., Synthesis of [2H3, 15N], [14C] Nexavar and its Labeled Metabolites, 49 Journal of Labelled Compounds and Radiopharmaceuticals 603 (2006).
Smart, Bruce, E., "Characteristics of C-F Systems," Organofluorine Chemistry Principles and Commercial Application, Chapter 3, pp. 57-88 (Plenum Press 1994).
Thornber, C.W., "Isosterism and Molecule Modification in Drug Design," 8 Chem. Soc. Rev. 563 (1979).
Welch, John, "The Effects of Selective Fluorination on Reactivity in Organic and Bioorganic Chemistry," Selective Fluorination in Organic and Bioorganic Chemistry 1 (Welch Ed., 1991).
Wermuth, C.G. et al., "Designing Prodrugs and Bioprecursors II: Bioprecursor Prodrugs," The Practice of Medicinal Chemistry, 1996, Academic Press Ltd., pp. 697-715.
Balant, L.P. et al.: "Metabolic Considerations in Prodrug Design." Burger's Medicinal Chemistry and Drug Discovery, 5th ed. John Wiley, New York, 1995: vol. 1, 949-982.
Berge, Stephen M, Lyle D. Bighley, and Donald C. Monkhouse. "Pharmaceutical Salts." The Journal of Pharmaceutical Science. Jan. 1977:1-19, vol. 66, No. 1.
Denny, William A. "Prodrug Strategies in Cancer Therapy." European Journal of Medicinal Chemistry. 2001: vol. 36, 577-595.
V. J. Stella et al.: "Prodrugs and Site-Specific Drug Delivery," Journal of Medicinal Chemistry, vol. 23, No. 12, Dec. 1980, pp. 1275-1282.
V. J. Stella et al: "Prodrugs Do they Have Advantages in Clinical Practice?" Drugs, vol. 29, 1985, pp. 455-473.
Roche, E.B. "Designs of Biopharmaceutical Properties Through Prodrugs and Analogs." American Pharmaceutical Association, Washington, D.C. 1977: 27-46.
Green et al, Protective Groups in Organic Synthesis, $3^{rd}$ Ed., John Wiley & Sons, New York, pp. xi-xii, 1999.
Byrn et al., "Pharmaceutical Solids: A Strategic Approach to Regulatory Considerations", Pharmaceutical Research, vol. 12, No. 7, 1995 (pp. 945-954).
Vippagunta et al., Advanced Drug Delivery Reviews 48 (2001) (pp. 3-26).
Rong Liu, "Water-insoluble Drug Formation", Interpharm Press (2000) (pp. 525-568).
L. Gatterman, "Preparation of Pure Organic Substances", 9 pages.
Bryn et al., "Pharmaceutical Solids: A Strategic Approach to Regulatory Considerations", Pharmaceutical Research, vol. 12, No. 7, pp. 945-954, 1995.
MacMahon et al., "Assay of 855 Test Chemicals in Ten Tester Strains Using a New Modification of the Ames Test for Bacterial Mutagens", Cancer Research 39, 682-693, Mar. 1979.
Rong Liu, "Water-Insolulable Drug Formation (2000)"Chapter 15; Alternation of the Solid State of the Drug Substance; Polymorphs, Solvates, and Amorphous forms, pp. 172-215.
Decision Rejecting the Opposition of Corresponding European Application No. 07 818583.2; dated Jul. 12, 2015.
Bauer, Fromming, Fuhrer, Lehrbuch der Pharmazeutischen Technologie, 8th Edistion 2006, Wissenschaftliche Verlagsgesellschaft Stuttgart, Chapter 7, pp. 216-219
European Medicines Agency (EMEA), Specifications: Test Procedures and Acceptance Criteria for New Drug Substances and New Drug Products: Chemical Substances, May 2000.
M. Bavin, Polymorphism in Process Development, Chemistry & Industry, 1989, pp. 527-529.
Morisette et al., High-throughput Crystallization: Polymorphs, Salts, Co-crystals, and Solvates of Pharmaceutical Solids, Advanced Drug Delivery Reviews, 2004, (56), pp. 275-300.
Jerry March, Advanced Organic Chemistry, 4th Edition, John Wiley, 1992, pp. 383-384.
P. G. Gassmann et al., Base Promoted Hydrolysis of Amides at Ambient Temperatures, J. Am. Chem. Soc., 1976, 98(5), pp. 1275-1276.
L. J. Ravin, Preformulation, Remington's Pharmaceutical Sciences, 17th Edition, Mack Publishing Company, 1985, Chapter 76, pp. 1409-1423.
Wikipedia Analysis, Sep. 14, 2015, Rick K. Aenar et al., 3 pages.
European Medicines Agency (EMEA), "Note for Guidance on Impurities Testing: Impurities in New Drug Substances", Oct. 2006.
International Conference on Harmonisation of Technical Requirements for Registration of Pharamaceuticals for Human Use (ICH), "Impurities in New Drug Substances Q3A(R2)", 25 Oct. 25, 2006.
Michael J. Jozwiakowski, Water Insoluble Drug Formulation, 2000, Interpharm Press Inc., Denver Co., Chapter 15 Alteration of the Solid State of the Drug Substance, pp. 525-568.

* cited by examiner

Fig 1: DSC- and TGA-thermograms of 4-[4-({[4-chloro-3-(trifluoromethyl)phenyl]carbamoyl}amino)-3-fluorophenoxy]-N-methylpyridine-2-carboxamide monohydrate and polymorph I
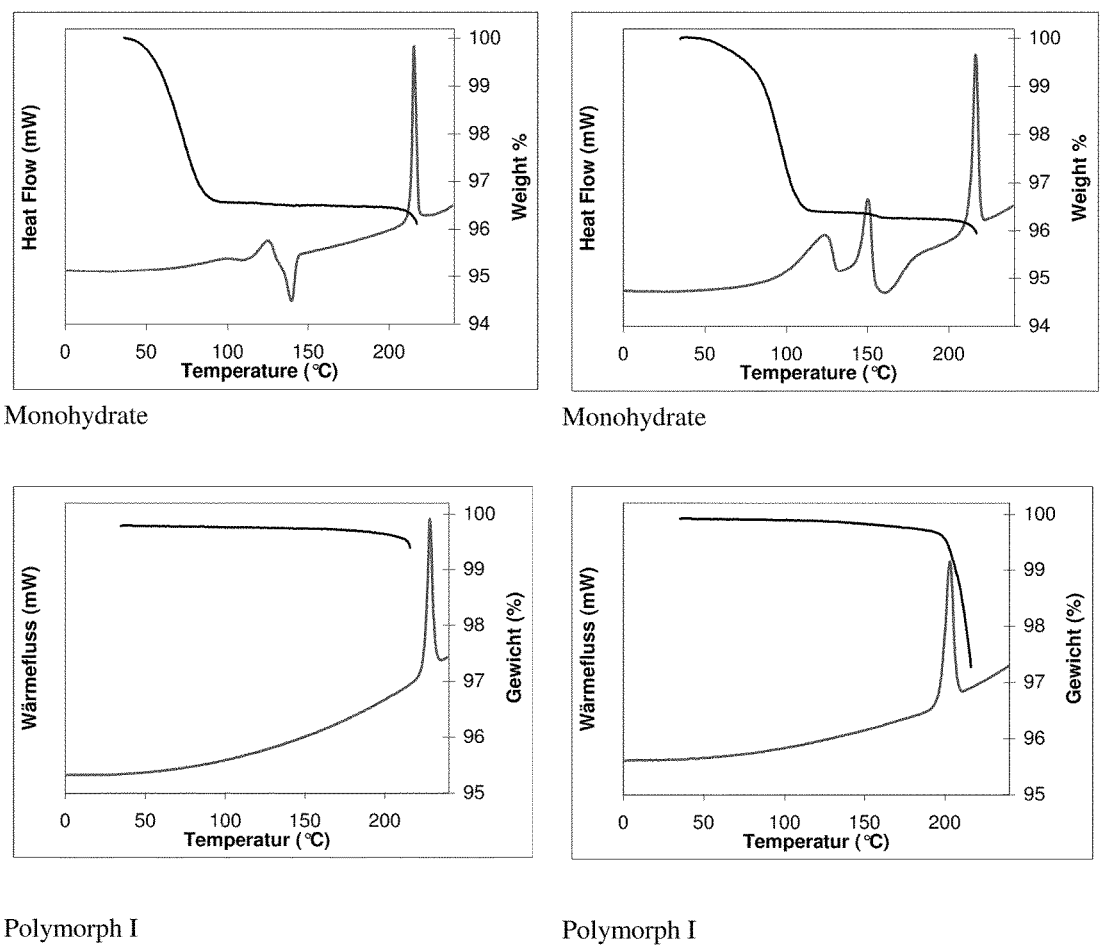
Monohydrate
Monohydrate
Polymorph I
Polymorph I Fig. 2: X-ray diffractograms of 4-[4-({[4-chloro-3-(trifluoromethyl)phenyl]carbamoyl}amino)-3-fluorophenoxy]-N-methylpyridine-2-carboxamide monohydrate (first) and polymorph I (second)
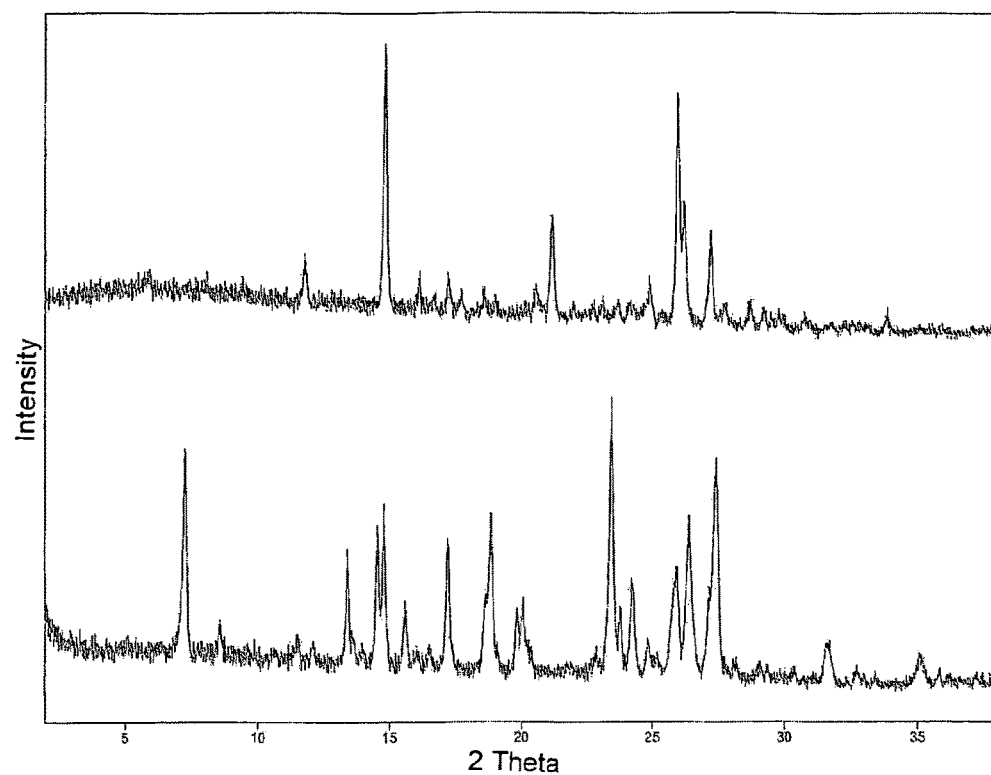

Fig. 3: IR spektra of 4-[4-({[4-chloro-3-(trifluoromethyl)phenyl]carbamoyl}amino)-3-fluorophenoxy]-N-methylpyridine-2-carboxamide monohydrate (first) and polymorph I (second)
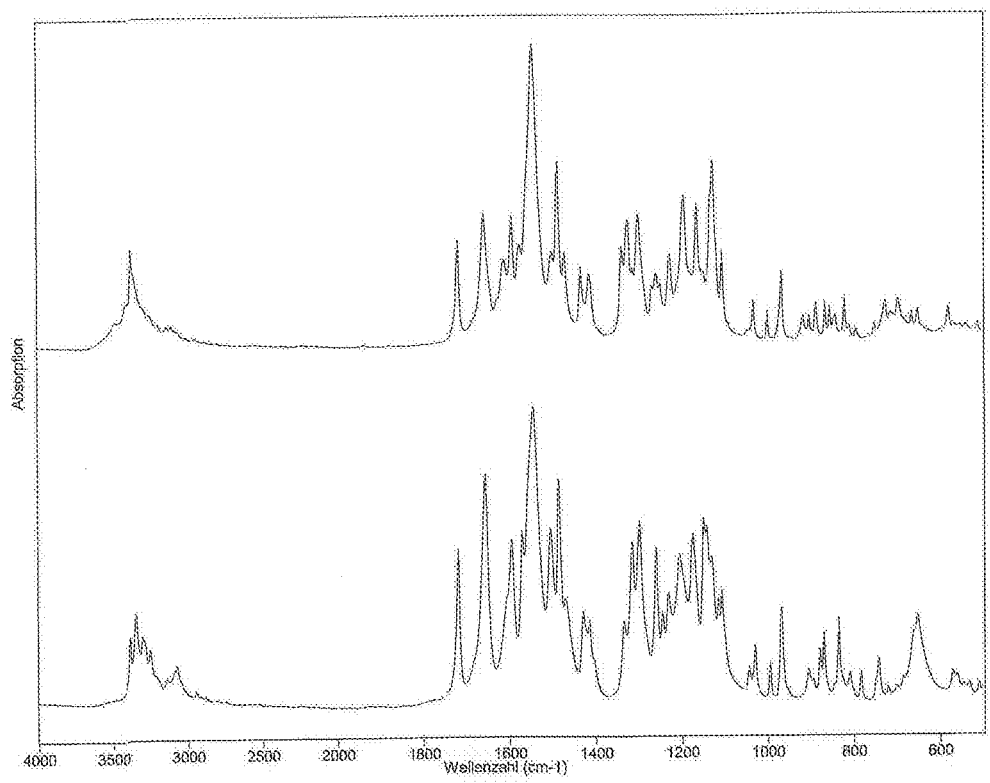

Fig. 4: Raman spektra of 4-[4-({[4-chloro-3-(trifluoromethyl)phenyl]carbamoyl}amino)-3-fluorophenoxy]-N-methylpyridine-2-carboxamide monohydrate (first) and polymorph I (second)
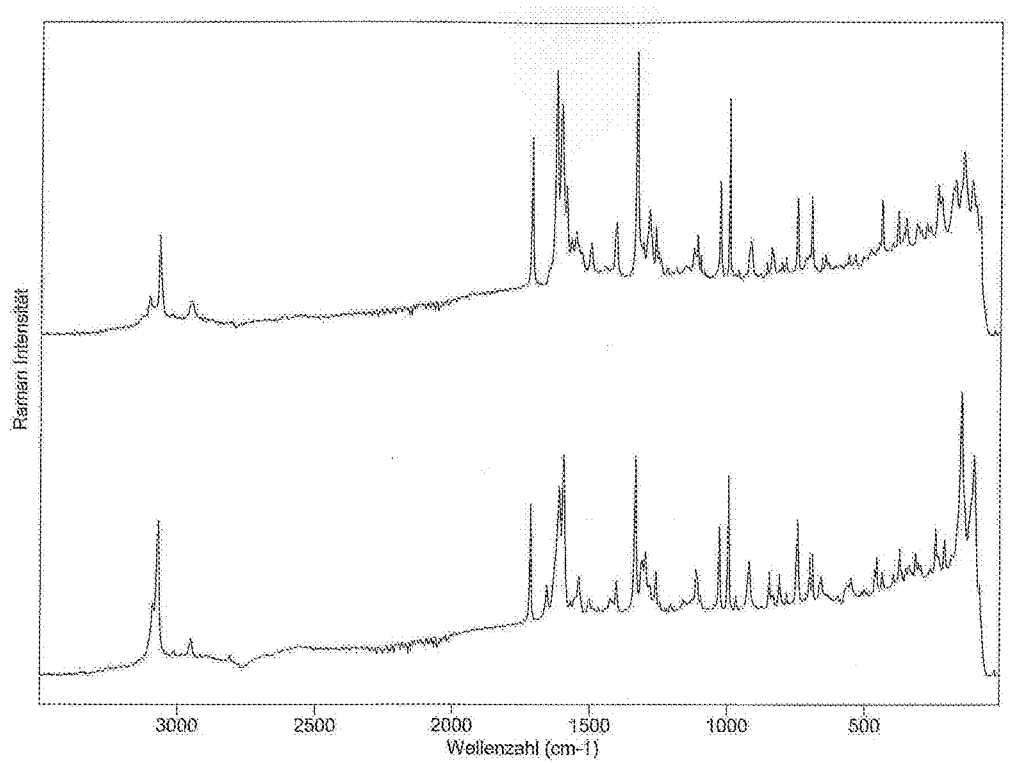

Fig. 5: FIR spektra of 4-[4-({[4-chloro-3-(trifluoromethyl)phenyl]carbamoyl}amino)-3-fluorophenoxy]-N-methylpyridine-2-carboxamide monohydrate (first) and polymorph I (second)
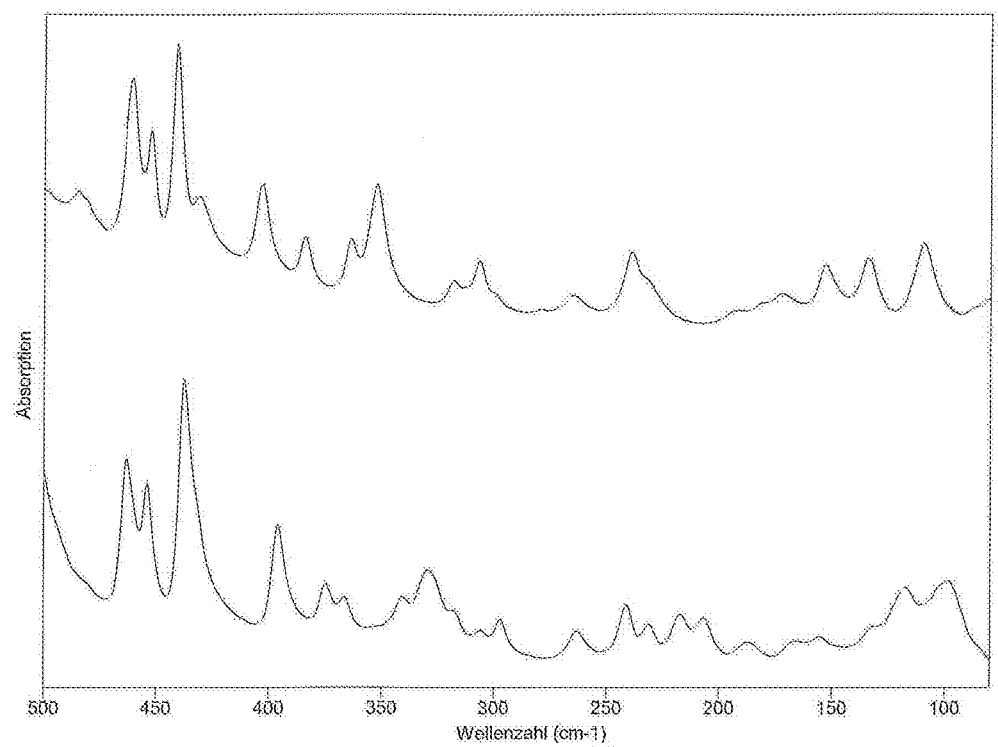

Fig. 6: NIR spektra of 4-[4-({[4-chloro-3-(trifluoromethyl)phenyl]carbamoyl}amino)-3-fluorophenoxy]-N-methylpyridine-2-carboxamide monohydrate (first) and polymorph I (second)
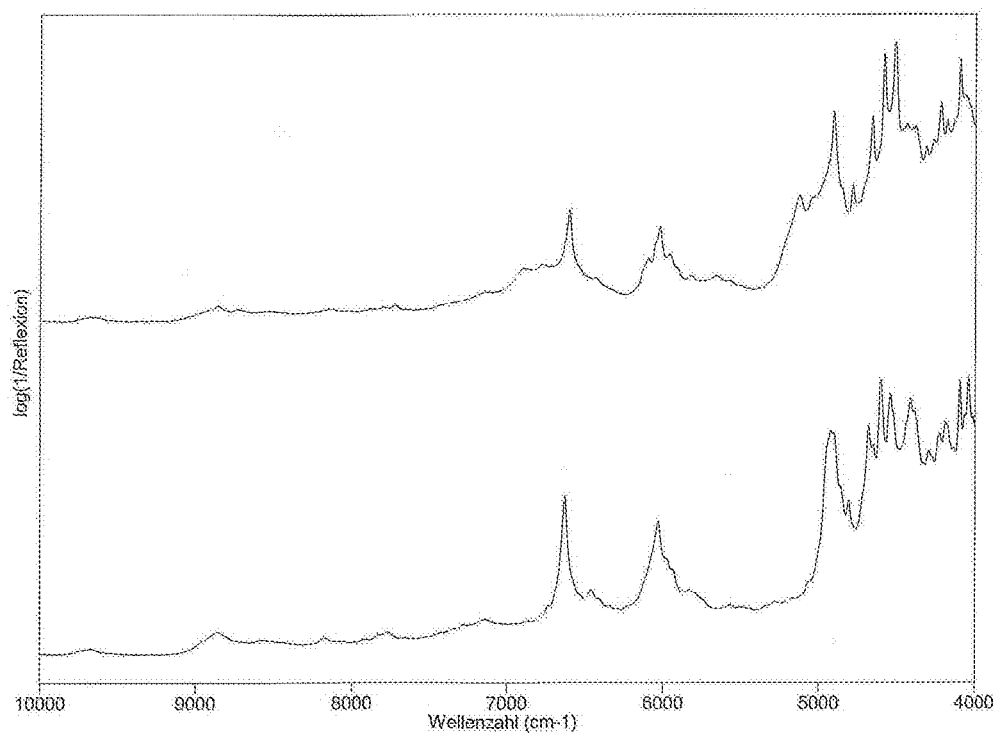

Fig. 7: $^{13}$C-solid state-NMR spektra of 4-[4-({[4-chloro-3-(trifluoromethyl)phenyl]carbamoyl}amino)-3-fluorophenoxy]-N-methylpyridine-2-carboxamide monohydrate (first) and polymorph I (second)
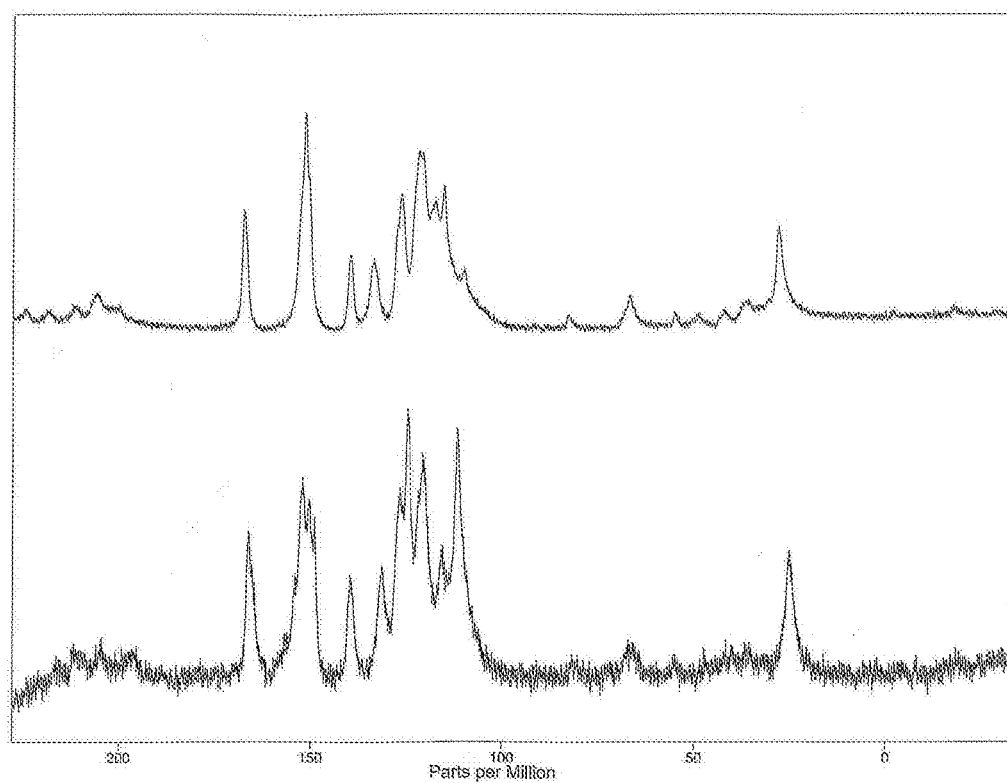

4-[4-({[4-CHLORO-3-(TRIFLUOROMETHYL) PHENYL]CARBAMOYL}AMINO)-3-FLUOROPHENOXY]-N-METHYLPYRIDINE-2-CARBOXAMIDE MONOHYDRATE

The present invention relates to 4-[4-({[4-chloro-3-(trifluoromethyl)phenyl]carbamoyl}amino)-3-fluorophenoxy]-N-methylpyridine-2-carboxamide monohydrate, to processes for its preparation, to pharmaceutical compositions comprising it and to its use in the control of disorders.

4-[4-({[4-chloro-3-(trifluoromethyl)phenyl]carbamoyl}amino)-3-fluorophenoxy]-N-methylpyridine-2-carboxamide is mentioned in WO 2005/009961 and corresponds to the compound of the formula (I):

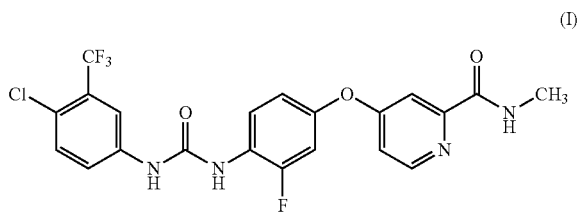 [SMILES: CNC(=O)c1cc(Oc2ccc(NC(=O)Nc3ccc(Cl)c(C(F)(F)F)c3)c(F)c2)ccn1]

(I)

WO 2005/009961 describes the compound of formula (I) as an inhibitor of the enzyme Raf kinase which may be used for the treatment of disorders in which angiogenesis and/or hyper-proliferation plays an important role, for example in tumor growth and cancer.

The compound of the formula (I) is prepared in the manner described in WO 2005/009961 and corresponds to a polymorph which in the following is named as polymorph I having a melting point of 186-206° C., a characteristic X-ray diffractogram, IR spectrum, Raman spectrum, FIR spectrum, NIR spectrum and a $^{13}$C-solid state-NMR spectrum (Tab. 2-7, FIG. 2-7).

The present invention provides the compound of the formula (I) in the monohydrate form which corresponds to the compound of the formula (II):

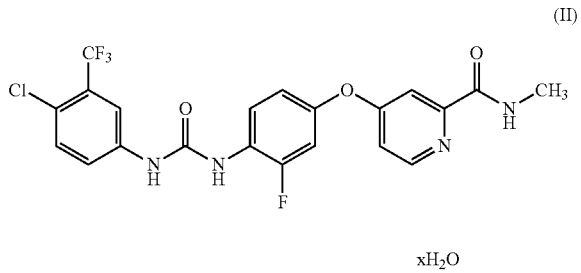 [SMILES: CNC(=O)c1cc(Oc2ccc(NC(=O)Nc3ccc(Cl)c(C(F)(F)F)c3)c(F)c2)ccn1]

(II)

xH$_2$O

The compound of the formula (II) contains water in an amount of 3.6% by weight. In comparison to the polymorph I of the compound of the formula (I), the compound of formula (II) has a clearly differentiable X-ray diffractogram, NIR spectrum, FIR spectrum, IR spectrum, $^{13}$C-solid state NMR spectrum and Raman spectrum (FIG. 2-7).

Surprisingly, the compound of the formula (II) shows a high stability in the manufacture of pharmaceutical compositions.

The inventive compound of the formula (II) is used in high purity in pharmaceutical formulations. For reasons of stability, a pharmaceutical formulation comprises the compound of the formula (II) mainly and no significant fractions of another form of the compound of the formula (I), for example of another polymorph of the compound of the formula (I). The pharmaceutical composition preferably contains more than 90 percent by weight, more preferably more than 95 percent by weight, of the compound of the formula (II) related to the total amount of the compound of the formula (II) present in the composition.

Method for Treatment:

The present invention also relates to a method for using the compound of the formula (II) and compositions thereof, to treat mammalian hyper-proliferative disorders. This method comprises administering to a mammal in need thereof, including a human, an amount of a compound of the formula (II) of this invention or composition thereof, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The present invention further provides the use of the compound of the formula (II) for the preparation of a pharmaceutical compositions for the treatment of the aforesaid disorders.

Combination with Other Pharmaceutical Agents:

The compound of the formula (II) of this invention can be administered as the sole pharmaceutical agent or in combination with one or more other pharmaceutical agents where the combination causes no unacceptable adverse effects. For example, the compound of the formula (II) of this invention can be combined with known anti-hyper-proliferative or other indication agents, and the like, as well as with admixtures and combinations thereof.

Optional anti-hyper-proliferative agents which can be added to the compositions include but are not limited to compounds listed on the cancer chemotherapy drug regimens in the 11$^{th}$ Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the compositions of the invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the compositions of the invention include but are not limited to other anti-cancer agents such as epothilone and its derivatives, irinotecan, raloxifen and topotecan.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

"Combination" mean for the purposes of the invention not only a dosage form which contains all the components (so-called fixed combinations), and combination packs containing the components separate from one another, but also components which are administered simultaneously or sequentially, as long as they are employed for the prophylaxis or treatment of the same disease.

The active ingredients of the combination according to the invention can be converted in a known manner into the usual formulations, which may be liquid or solid formulations. Examples are tablets, coated tablets, pills, capsules, granules, aerosols, syrups, emulsions, suspensions, solutions.

Since the combination according to the invention is well tolerated and in some cases is effective even in low dosages, a wide range of formulation variants is possible. Thus, one possibility is to formulate the individual active ingredients of the combination according to the invention separately. In this case, it is not absolutely necessary for the individual active ingredients to be taken at the same time; on the contrary, sequential intake may be advantageous to achieve optimal effects. It is appropriate with such separate administration to combine the formulations of the individual active ingredients, for example tablets or capsules, simultaneously together in a suitable primary packaging. The active ingredients are present in the primary packaging in each case in separate containers which may be, for example, tubes, bottles or blister packs. Such separate packaging of the components in the joint primary packaging is also referred to as a kit.

Further formulation variants which are suitable and preferred for the combination according to the invention are also fixed combinations. "Fixed combination" is intended here to mean pharmaceutical forms in which the components are present together in a fixed ratio of amounts. Such fixed combinations may be, for example, in the form of oral solutions, but they are preferably solid oral pharmaceutical preparations, e.g. capsules or tablets.

Pharmaceutical Compositions:

This invention also relates to pharmaceutical compositions containing the compound of the formula (II) of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions which are comprised of a pharmaceutically acceptable carrier and a pharmaceutically effective amount of a compound of the formula (II) of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compound of the formula (II) of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compound of the formula (II) can be formulated into solid or liquid preparations such as solid dispersion, capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compound of the formula (II) of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compound of the formula (II) of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A compositions of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material is, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The pharmaceutical compositions of this invention may also be in the form of a solid dispersion. The solid dispersion may be a solid solution, glass solution, glass suspension, amorphous precipitation in a crystalline carrier, eutectic or monotecic, compound or complex formation and combinations thereof.

An aspect of the invention of particular interest is a pharmaceutical composition comprising a solid dispersion, wherein the matrix comprises a pharmaceutically acceptable polymer, such as polyvinylpyrrolidone, vinylpyrrolidone/vinylacetate copolymer, polyalkylene glycol (i.e. polyethylene glycol), hydroxyalkyl cellulose (i.e. hydroxypropyl cellulose), hydroxyalkyl methyl cellulose (i.e. hydroxypropyl methyl cellulose), carboxymethyl cellulose, sodium carboxymethyl cellulose, ethyl cellulose, polymethacrylates, polyvinyl alcohol, polyvinyl acetate, vinyl alcohol/vinyl acetate copolymer, polyglycolized glycerides, xanthan gum, carrageenan, chitosan, chitin, poyldextrin, dextrin, starch and proteins.

Another aspect of the invention is a pharmaceutical composition comprising a solid dispersion, wherein the matrix comprises a sugar and/or sugar alcohol and/or cyclodextrin, for example sucrose, lactose, fructose, maltose, raffinose, sorbitol, lactitol, mannitol, maltitol, erythritol, inositol, trehalose, isomalt, inulin, maltodextrin, β-cyclodextrin, hydroxypropyl-β-cyclodextrin or sulfobutyl ether cyclodextrin.

Additional suitable carriers that are useful in the formation of the matrix of the solid dispersion include, but are not limited to alcohols, organic acids, organic bases, amino acids, phospholipids, waxes, salts, fatty acid esters, polyoxyethylene sorbitan fatty acid esters, and urea.

The solid dispersion of the compound of formula (II) in the matrix may contain certain additional pharmaceutical acceptable ingredients, such as surfactants, fillers, disintegrants, recrystallization inhibitors, plasticizers, defoamers, antioxidants, detackifier, pH-modifiers, glidants and lubricants.

The solid dispersion of the invention is prepared according to methods known to the art for the manufacture of solid dispersions, such as fusion/melt technology, hot melt extrusion, solvent evaporation (i.e. freeze drying, spray drying or layering of powders of granules), coprecipitation, supercritical fluid technology and electrostatic spinning method.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients which can be used as appropriate to formulate the composition for its intended route of administration include:

- acidifying agents (examples include but are not limited to acetic acid, citric acid, fumaric acid, hydrochloric acid, nitric acid);
- alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);
- adsorbents (examples include but are not limited to powdered cellulose and activated charcoal);
- aerosol propellants (examples include but are not limited to carbon dioxide, $CCl_2F_2$, $F_2ClC-CClF_2$ and $CClF_3$)
- air displacement agents (examples include but are not limited to nitrogen and argon);
- antifungal preservatives (examples include but are not limited to benzoic acid, butylparaben, ethylparaben, methylparaben, propylparaben, sodium benzoate);
- antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);
- antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);
- binding materials (examples include but are not limited to block polymers, natural and synthetic rubber, polyacrylates, polyurethanes, silicones, polysiloxanes and styrene-butadiene copolymers);
- buffering agents (examples include but are not limited to potassium metaphosphate, dipotassium phosphate, sodium acetate, sodium citrate anhydrous and sodium citrate dihydrate)
- carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)
- chelating agents (examples include but are not limited to edetate disodium and edetic acid)
- colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);
- clarifying agents (examples include but are not limited to bentonite);
- emulsifying agents (examples include but are not limited to acacia, cetomacrogol, cetyl alcohol, glyceryl monostearate, lecithin, sorbitan monooleate, polyoxyethylene 50 monostearate);
- encapsulating agents (examples include but are not limited to gelatin and cellulose acetate phthalate)
- flavorants (examples include but are not limited to anise oil, cinnamon oil, cocoa, menthol, orange oil, peppermint oil and vanillin);
- humectants (examples include but are not limited to glycerol, propylene glycol and sorbitol);
- levigating agents (examples include but are not limited to mineral oil and glycerin);
- oils (examples include but are not limited to arachis oil, mineral oil, olive oil, peanut oil, sesame oil and vegetable oil);
- ointment bases (examples include but are not limited to lanolin, hydrophilic ointment, polyethylene glycol ointment, petrolatum, hydrophilic petrolatum, white ointment, yellow ointment, and rose water ointment);
- penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)
- plasticizers (examples include but are not limited to diethyl phthalate and glycerol);
- solvents (examples include but are not limited to ethanol, corn oil, cottonseed oil, glycerol, isopropanol, mineral oil, oleic acid, peanut oil, purified water, water for injection, sterile water for injection and sterile water for irrigation);
- stiffening agents (examples include but are not limited to cetyl alcohol, cetyl esters wax, microcrystalline wax, paraffin, stearyl alcohol, white wax and yellow wax);
- suppository bases (examples include but are not limited to cocoa butter and polyethylene glycols (mixtures));
- surfactants (examples include but are not limited to benzalkonium chloride, nonoxynol 10, oxtoxynol 9, polysorbate 80, sodium lauryl sulfate and sorbitan monopalmitate);
- suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);
- sweetening agents (examples include but are not limited to aspartame, dextrose, glycerol, mannitol, propylene glycol, saccharin sodium, sorbitol and sucrose);
- tablet anti-adherents (examples include but are not limited to magnesium stearate and talc);
- tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
- tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
- tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);
- tablet direct compression excipients (examples include but are not limited to dibasic calcium phosphate);
- tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);
- tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnauba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithin, sorbitol monooleate, polyoxyethylene sorbitol monooleate, and polyoxyethylene stearate).

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Pharmaceutical compositions according to the present invention can be illustrated as follows:

Sterile IV Solution: A 5 mg/ml solution of the desired compound of this invention is made using sterile, injectable water, and the pH is adjusted if necessary. The solution is diluted for administration to 1-2 mg/ml with sterile 5% dextrose and is administered as an IV infusion over 60 minutes.

Lyophilized powder for IV administration: A sterile preparation can be prepared with (i) 100-1000 mg of the desired compound of this invention as a lypholized powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular suspension: The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dosage of the Pharmaceutical Compositions of the Present Invention:

Based upon standard laboratory techniques known to evaluate compounds useful for the treatment of hyperproliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg, and preferably from about 0.01 mg/kg to about 20 mg/kg body weight per day. A unit dosage may contain from about 0.5 mg to about 1500 mg of active ingredient, and can be administered one or more times per day. The daily dosage for administration by injection, including intravenous, intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.1 to 200 mg administered between one to four times daily. The transdermal concentration will preferably be that required to maintain a daily dose of from 0.01 to 200 mg/kg. The daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Process for Preparing:

The invention further provides a process for preparing the compound of the formula (II) by dissolution of the compound of the formula (I) e.g. in the polymorph I, obtained as described in WO 2005/009961, in an inert solvent and adding water until the compound of the formula (II) precipitates. The compound of the formula (II) is thus obtained.

The invention likewise provides a process for preparing the compound of the formula (II) by suspending the compound of the formula (I) e.g. in the polymorph I, obtained as described WO 2005/009961, in an aqueous solvent and then stiffing or shaking until the desired degree of conversion is attained. The crystals are isolated and dried. The compound of the formula (II) is thus obtained.

Suitable inert solvents are lower alcohols, for example methanol, ethanol, n-propanol, isopropanol, n-butanol, sec-butanol, isobutanol, 1-pentanol or ketones such as acetone, or alkanes such as n-pentane, cyclopentane, n-hexane, cyclohexane, or tetrahydrofuran, or acetonitrile, or toluene, or ethyl acetate, or 1,4-dioxan or mixtures of the solvents mentioned, or mixtures of the solvents mentioned with water. Preference is given to acetone, methanol, ethanol, mixtures of the solvents mentioned.

Preference is given to preparing the compound of the formula (II) by solving the compound of the formula (I) in the polymorph I, obtained as described in WO 2005/009961, in ethanol and adding water until the compound of the formula (II) precipitates. The compound of the formula (II) is thus obtained.

Preference is likewise given to preparing the compound of the formula (II) by suspending the compound of the formula (I) in the polymorph I, obtained as described WO 2005/009961, in an aqueous solvent and then stirring or shaking until the desired degree of conversion is attained at a temperature of 25° C. The crystals are isolated and dried. The compound of the formula (II) is thus obtained.

The processes are generally carried out at atmospheric pressure. However, it is also possible to work at elevated pressure or at reduced pressure (for example in a range of from 0.5 to 5 bar).

It is believed that one skilled in the art, using the preceding information and information available in the art, can utilize the present invention to its fullest extent.

It should be apparent to one of ordinary skill in the art that changes and modifications can be made to this invention without departing from the spirit or scope of the invention as it is set forth herein.

All publications, applications and patents cited above and below are incorporated herein by reference.

The weight data in the tests and examples which follow are, unless stated otherwise, percentages by weight; parts are parts by weight. Solvent ratios, dilution ratios and concentration data of liquid/liquid solutions are based on each case on the volume.

WORKING EXAMPLES

The thermograms are obtained using a DSC 7 or Pyris-1 differential scanning calorimeter and TGA 7 thermogravimetric analyzer from Perkin-Elmer. The X-ray diffractograms are registered in a Stoe transmission diffractometer. The IR, FIR, MR and Raman spectra are recorded using IFS 66v (IR, FIR), IFS 28/N (NIR) and RFS 100 (Raman) Fourier spectrometers from Bruker. The $^{13}C$-solid state NMR spectra are recorded using the NMR spectrometer DRX400 from Bruker.

Example 1

Preparation of 4-[4-({[4-chloro-3-(trifluoromethyl) phenyl]carbamoyl}amino)-3-fluorophenoxy]-N-methylpyridine-2-carboxamide monohydrate Example 1.1

400 mg of 4-[4-({[4-chloro-3-(trifluoromethyl)phenyl] carbamoyl}amino)-3-fluorophenoxy]-N-methylpyridine-2-carboxamide in the polymorph I, prepared as described in WO 2005/009961, are dissolved in acetone and the solution is filtered. Water is added to one fourth of the filtrate until precipitation. The precipitate is filtered and dried at room temperature under ambient humidity. The sample is tested gravimetrically and corresponds to the title compound.

Example 1.2

400 mg of 4-[4-({[4-chloro-3-(trifluoromethyl)phenyl] carbamoyl}amino)-3-fluorophenoxy]-N-methylpyridine-2-carboxamide in the polymorph I, prepared as described in WO 2005/009961, are dissolved in 50 ml of ethanol and the solution is filtered. One fourth of the solution is stayed in the freezer for crystallization at about −20° C. until the solvent is evaporated. The residue is tested by X-ray diffractometry and corresponds to the title compound.

Example 1.3

100 mg of 4-[4-({[4-chloro-3-(trifluoromethyl)phenyl] carbamoyl}amino)-3-fluorophenoxy]-N-methylpyridine-2-carboxamide in the polymorph I, prepared as described in WO 2005/009961, are suspended in 2 ml of a mixture of acetonitril-water (1:1) and shaken at 25° C. After one week the suspension is filtered and the residue is dried at room temperature and ambient humidity. The residue is tested gravimetrically and corresponds to the title compound.

Example 1.4

100 mg of 4-[4-({[4-chloro-3-(trifluoromethyl)phenyl] carbamoyl}amino)-3-fluorophenoxy]-N-methylpyridine-2-carboxamide in the polymorph I, prepared as described in WO 2005/009961, are suspended in 2 ml of a mixture of tetrahydrofuran-water (1:1) and stirred at 10° C. After two weeks the suspension is filtered and the residue is dried at room temperature and ambient humidity. The residue is tested by X-ray diffractometry and corresponds to the title compound.

BRIEF DESCRIPTION OF THE DRAWING

FIG. 1 is a DSC- and TGA-thermogram of 4-[4-({[4-chloro-3-(trifluoromethyl)phenyl]carbamoyl}amino)-3-fluorophenoxy]-N-methylpyridine-2-carboxamide monohydrate and a DSC- and TGA-thermogram of the polymorph I.

FIG. 2 is a X-ray diffractogram of 4-[4-({[4-chloro-3-(trifluoromethyl)phenyl]carbamoyl}amino)-3-fluorophenoxy]-N-methylpyridine-2-carboxamide monohydrate (first) and a X-ray diffractogram of polymorph I (second).

FIG. 3 is an IR spectrum of 4-[4-({[4-chloro-3-(trifluoromethyl)phenyl]carbamoyl}amino)-3-fluorophenoxy]-N-methylpyridine-2-carboxamide monohydrate (first) and an IR spectrum of polymorph I (second)

FIG. 4 is a Raman spectrum of 4-[4-({[4-chloro-3-(trifluoromethyl)phenyl]carbamoyl}amino)-3-fluorophenoxy]-

N-methylpyridine-2-carboxamide monohydrate (first) and a Raman spectrum of polymorph I (second).

FIG. 5 is a FIR spectrum of 4-[4-({[4-chloro-3-(trifluoromethyl)phenyl]carbamoyl}amino)-3-fluorophenoxy]-N-methylpyridine-2-carboxamide monohydrate (first) and a FIR spectrum of polymorph I (second).

FIG. 6 is a NIR spectrum of 4-[4-({[4-chloro-3-(trifluoromethyl)phenyl]carbamoyl}amino)-3-fluorophenoxy]-N-methylpyridine-2-carboxamide monohydrate (first) and a NIR spectrum of polymorph I (second).

FIG. 7 is a $^{13}$C-solid state-NMR spectrum of 4-[4-({[4-chloro-3-(trifluoromethyl)phenyl]carbamoyl}amino)-3-fluorophenoxy]-N-methylpyridine-2-carboxamide monohydrate (first) and a $^{13}$C-solid state-NMR spectrum of polymorph I (second).

TABLE 1

Differential Scanning Calorimetry and Thermogravimetry

| | Monohydrate | Polymorph I |
|---|---|---|
| Melting point [° C.] | — | 186-206 |
| Loss in mass [% by wt.] | 3.6 | <0.4 |

TABLE 2

X-ray diffractometry
Peak maxima [2 Theta]

| Monohydrate | Polymorph I |
|---|---|
| 5.9 | 7.2 |
| 8.1 | 7.3 |
| 9.5 | 8.6 |
| 11.8 | 10.7 |
| 14.9 | 11.5 |
| 16.2 | 12.1 |
| 16.7 | 13.4 |
| 17.2 | 13.6 |
| 17.7 | 14.0 |
| 18.6 | 14.5 |
| 19.0 | 14.8 |
| 20.5 | 15.6 |
| 20.8 | 16.0 |
| 21.2 | 16.5 |
| 22.0 | 17.2 |
| 22.2 | 18.6 |
| 22.4 | 18.8 |
| 22.8 | 19.1 |
| 23.1 | 19.8 |
| 23.7 | 20.1 |
| 24.1 | 20.2 |
| 24.3 | 20.4 |
| 24.7 | 21.8 |
| 24.9 | 22.9 |
| 26.0 | 23.5 |
| 26.2 | 23.8 |
| 26.3 | 24.2 |
| 27.1 | 24.9 |
| 27.2 | 25.2 |
| 27.6 | 25.9 |
| 27.8 | 26.0 |
| 28.7 | 26.4 |
| 29.2 | 26.6 |
| 30.8 | 27.2 |
| | 27.4 |
| | 28.2 |
| | 29.1 |
| | 29.4 |
| | 30.4 |
| | 30.9 |
| | 31.6 |
| | 32.7 |
| | 33.0 |
| | 33.4 |

TABLE 2-continued

X-ray diffractometry
Peak maxima [2 Theta]

| Monohydrate | Polymorph I |
|---|---|
| | 35.1 |
| | 35.3 |
| | 35.8 |
| | 36.1 |
| | 36.6 |
| | 37.3 |

TABLE 3

IR spectroscopy
Peak maxima [cm$^{-1}$]

| Monohydrate | Polymorph I |
|---|---|
| 509 | 512 |
| 536 | 535 |
| 577 | 563 |
| 648 | 572 |
| 662 | 654 |
| 694 | 722 |
| 710 | 744 |
| 723 | 785 |
| 749 | 811 |
| 792 | 836 |
| 807 | 871 |
| 817 | 880 |
| 839 | 906 |
| 852 | 970 |
| 863 | 996 |
| 884 | 1030 |
| 900 | 1044 |
| 914 | 1108 |
| 964 | 1116 |
| 997 | 1131 |
| 1029 | 1143 |
| 1102 | 1151 |
| 1123 | 1176 |
| 1146 | 1207 |
| 1162 | 1233 |
| 1192 | 1246 |
| 1225 | 1261 |
| 1247 | 1300 |
| 1256 | 1317 |
| 1266 | 1336 |
| 1298 | 1416 |
| 1311 | 1431 |
| 1323 | 1471 |
| 1336 | 1487 |
| 1411 | 1506 |
| 1431 | 1546 |
| 1469 | 1572 |
| 1485 | 1596 |
| 1498 | 1657 |
| 1544 | 1720 |
| 1573 | 3077 |
| 1591 | 3255 |
| 1609 | 3306 |
| 1656 | 3350 |
| 1716 | 3389 |
| 3108 | |
| 3252 | |
| 3375 | |

TABLE 4

| Raman spectroscopy Peak maxima [cm$^{-1}$] | |
|---|---|
| Monohydrate | Polymorph I |
| 85 | 85 |
| 116 | 105 |
| 146 | 151 |
| 176 | 213 |
| 186 | 245 |
| 228 | 317 |
| 241 | 340 |
| 281 | 352 |
| 318 | 375 |
| 356 | 397 |
| 385 | 438 |
| 443 | 457 |
| 541 | 465 |
| 564 | 551 |
| 649 | 659 |
| 661 | 691 |
| 698 | 701 |
| 750 | 746 |
| 793 | 786 |
| 807 | 811 |
| 844 | 849 |
| 861 | 921 |
| 920 | 970 |
| 997 | 997 |
| 1031 | 1030 |
| 1103 | 1099 |
| 1116 | 1111 |
| 1128 | 1116 |
| 1258 | 1209 |
| 1267 | 1261 |
| 1290 | 1284 |
| 1313 | 1300 |
| 1336 | 1314 |
| 1410 | 1336 |
| 1501 | 1405 |
| 1556 | 1427 |
| 1573 | 1504 |
| 1592 | 1541 |
| 1610 | 1597 |
| 1628 | 1613 |
| 1715 | 1657 |
| 2951 | 1717 |
| 3069 | 2951 |
| 3104 | 3071 |
| | 3090 |

TABLE 5

| FIR spectroscopy Peak maxima [cm$^{-1}$] | |
|---|---|
| Monohydrate | Polymorph I |
| 109 | 99 |
| 134 | 117 |
| 153 | 155 |
| 172 | 166 |
| 191 | 187 |
| 239 | 207 |
| 265 | 217 |
| 307 | 231 |
| 318 | 241 |
| 353 | 263 |
| 364 | 297 |
| 384 | 306 |
| 403 | 318 |
| 431 | 329 |
| 441 | 341 |
| 453 | 367 |
| 461 | 375 |
| 485 | 396 |
| | 438 |

TABLE 5-continued

| FIR spectroscopy Peak maxima [cm$^{-1}$] | |
|---|---|
| Monohydrate | Polymorph I |
| | 454 |
| | 463 |

TABLE 6

| NIR spectroscopy Peak maxima [cm$^{-1}$] | |
|---|---|
| Monohydrate | Polymorph I |
| 4097 | 4041 |
| 4221 | 4098 |
| 4512 | 4190 |
| 4584 | 4230 |
| 4660 | 4296 |
| 4784 | 4414 |
| 4906 | 4542 |
| 5127 | 4604 |
| 6025 | 4681 |
| 6605 | 4808 |
| | 4924 |
| | 6033 |
| | 6632 |
| | 8858 |

TABLE 7

| $^{13}$C-solid state-NMR spectroscopy Peak maxima [ppm] | |
|---|---|
| Monohydrate | Polymorph I |
| 28 | 25 |
| 110 | 105 |
| 115 | 112 |
| 117 | 116 |
| 121 | 121 |
| 126 | 125 |
| 133 | 127 |
| 139 | 131 |
| 151 | 139 |
| 167 | 149 |
| | 150 |
| | 152 |
| | 166 |

What is claimed is:

1. A compound of the formula (II)

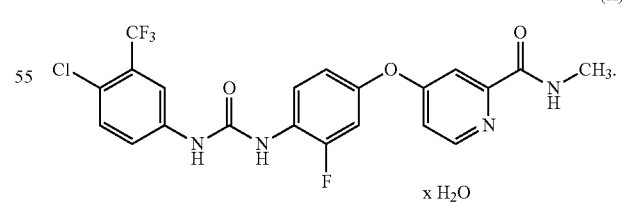

2. A pharmaceutical composition comprising a compound of claim 1 and one or more pharmaceutically suitable excipients for the treatment of solid tumors, lymphomas, sarcomas, leukemias, cancers of the breast, respiratory tract, brain, reproductive organs, digestive tract, urinary tract, eye, liver, skin, head and neck, thyroid and/or parathyroid.

3. A method for the treatment of a hyper-proliferative disorder comprising administering an effective amount of a pharmaceutical composition of claim 2 to a subject in need thereof.

4. The method of claim 3 wherein the hyper-proliferative disorder to be treated is a solid tumor, lymphoma, sarcoma, leukemia or cancer of the breast, respiratory tract, brain, reproductive organs, digestive tract, urinary tract, eye, liver, skin, head and neck, thyroid or parathyroid.

5. A pharmaceutical composition comprising the compound of the formula (II) of claim 1 and one or more inert, nontoxic, pharmaceutically suitable excipients.

6. A method for treating hyper-proliferative disorders comprising administering an effective amount of a pharmaceutical composition of claim 5 to a subject in need thereof.

7. A combination comprising the compound of the formula (II) of claim 1 and one or more other pharmaceutical agents.

8. The combination of claim 7 wherein the one or more other pharmaceutical agents are cytotoxic agents, signal transduction inhibitors, anti-cancer agents, or antiemetics.

9. The pharmaceutical composition of claim 5 comprising one or more other pharmaceutical agents.

10. The pharmaceutical composition of claim 9 wherein the one or more other pharmaceutical agents are anti-hyper-proliferative agents, cytotoxic agents, signal transduction inhibitors, anti-cancer agents and/or antiemetics.

11. A pharmaceutical composition comprising a compound of claim 1 of the formula (II) and a pharmaceutically suitable excipient for the treatment of hyper-proliferative disorders.

12. A process for the preparation of the compound of the formula (II)

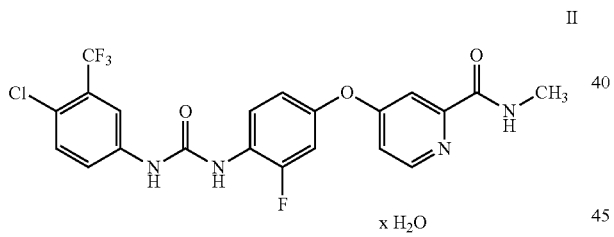

which comprises dissolution of 4-[4-({[4-chloro-3-(trifluoromethyl)phenyl]carbamoyl{amino) -3-fluorophenoxy]-N-methylpyridine-2-carboxamide in an inert solvent and adding water until precipitation.

13. A process for the preparation of the compound of the formula (II)

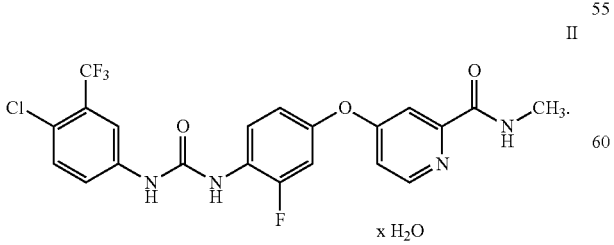

which comprises suspension of 4-[4-({[4-chloro-3-(trifluoromethyl)phenyl]carbamoyl}amino) -3-fluorophenoxy]-N-methylpyridine-2-carboxamide in an aqueous solvent and then stirring or shaking until conversion to the compound of the formula (II).

14. A pharmaceutical composition comprising a compound of claim 1 of the formula (II) and a pharmaceutically suitable excipient for the treatment of tumors of the digestive tract.

15. A pharmaceutical composition comprising a compound of claim 1 of the formula (II) and a pharmaceutically suitable excipient for the treatment of colorectal cancer.

16. A method for the treatment of tumors of the digestive tract comprising administering an effective amount of a pharmaceutical composition of claim 14 to a subject in need thereof.

17. A method for the treatment of colorectal cancer comprising administering an effective amount of a pharmaceutical composition of claim 15 to a subject in need thereof.

18. A method of claim 4 wherein the cancer of the breast is invasive ductal carcinoma, invasive lobular carcinoma, ductal carcinoma in situ, or lobular carcinoma in situ;

cancer of the respiratory tract is small-cell and non-small-cell lung carcinoma, bronchial adenoma or pleuropulmonary blastoma;

cancer of the brain is brain stem glioma, hypophtalmic glioma, cerebellar astrocytoma, cerebral astrocytoma, medulloblastoma, ependymoma, neuroectodermal tumor or pineal tumor;

cancer of the male reproductive organ is prostate cancer, testicular cancer, endometrial cancer, cervical cancer, ovarian cancer, vaginal cancer, vulvar cancer or sarcoma of the uterus;

cancer of the digestive tract is anal cancer, colon cancer, colorectal cancer, esophageal cancer, gallbladder cancer, gastric cancer, pancreatic cancer, rectal cancer, small intestine cancer or salivary gland cancer;

cancer of the urinary tract is bladder cancer, penile cancer, kidney cancer, renal pelvis cancer, ureter cancer or urethral cancer;

cancer of the eye is intraocular melanoma or retinoblastoma;

cancer of the liver is hepatocellular carcinoma (liver cell carcinomas with or without fibrolarnellar variant), cholangiocarcinoma (intrahepatic bile duct carcinoma), or mixed hepatocellular cholangiocarcinoma;

cancer of the skin is squamous cell carcinoma, Kaposi's sarcoma, malignant melanoma, Merkel cell skin cancer, or non-melanoma skin cancer;

cancer of the head-and-neck is laryngeal cancer, hypopharyngeal cancer, nasopharyngeal cancer, oropharyngeal cancer, lip cancer or oral cavity cancer;

the lymphoma is AIDS-related lymphoma, non-Hodgkin's lymphoma, cutaneous T-cell lymphoma, Hodgkin's disease, or lymphoma of the central nervous system;

the Sarcoma is sarcoma of the soft tissue, osteosarcoma, malignant fibrous histiocytoma, lymphosarcoma, or rhabdomyosarcoma;

the Leukemia is acute myeloid leukemia, acute lymphoblastic leukemia, chronic lymphocytic leukemia, chronic myelogenous leukemia, or hairy cell leukemia.

19. The compound of the formula (II)

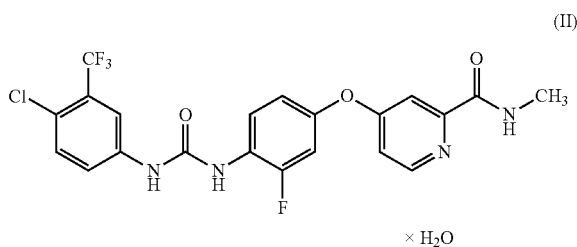 [SMILES: CNC(=O)c1cc(Oc2ccc(NC(=O)Nc3ccc(Cl)c(C(F)(F)F)c3)c(F)c2)ccn1]

× H₂O which shows in the X-ray diffractometry a peak maximum of the 2 Theta angle of 21.2.

20. The compound of claim 19 which shows in the FIR spectrum a peak maximum of 353 cm$^{-1}$.

21. A pharmaceutical composition comprising a compound of claim 20 and one or more pharmaceutically suitable excipients for the treatment of solid tumors, lymphomas, sarcomas, leukaemia's, cancers of the breast, respiratory tract, brain, reproductive organs, digestive tract, urinary tract, eye, liver, skin, head and neck, thyroid and/or parathyroid.

22. A method for the treatment of a hyper-proliferative disorder comprising administering an effective amount of a pharmaceutical composition of claim 21 to a subject in need thereof.

23. A method for the treatment of tumors of the digestive tract comprising administering an effective amount of a pharmaceutical composition of claim 21 to a subject in need thereof.

24. A method for the treatment of colorectal cancer comprising administering an effective amount of a pharmaceutical composition of claim 21 to a subject in need thereof.

25. A compound of the formula (II) of claim 1 which contains H₂O in an amount of 3.6% by weight.

26. A pharmaceutical composition according to claim 2 wherein the pharmaceutically suitable excipient is water.

27. A pharmaceutical composition according to claim 26 which is a sterile injectable aqueous suspension.

28. A pharmaceutical composition according to claim 2 wherein the pharmaceutically suitable excipient is selected from vegetable oil, arachis oil, olive oil, sesame oil, coconut oil, mineral oil and liquid paraffin.

29. A pharmaceutical composition according to claim 28 which is an oily suspension.

* * * * *